(12) United States Patent
Doeberitz et al.

(10) Patent No.: US 7,569,538 B2
(45) Date of Patent: Aug. 4, 2009

(54) IMMUNIZATION OF AN INDIVIDUAL AGAINST CARCINOMAS AND THE PRELIMINARY STAGES THEREOF

(76) Inventors: Magnus Von Knebel Doeberitz, Im Neuenheimer Feld 110, Heidelberg (DE) 69120; Michael Linnebacher, Zum Klopp23, Stennweiler (DE) 66578; Wolfgang Rudy, Albert-Einstein-Strasse 76, Bretten (DE) 75015

( * ) Notice: Subject to any disclaimer, the term of this patent is extended or adjusted under 35 U.S.C. 154(b) by 0 days.

(21) Appl. No.: 11/433,386

(22) Filed: May 15, 2006

(65) Prior Publication Data
US 2006/0210591 A1 Sep. 21, 2006

Related U.S. Application Data

(63) Continuation of application No. 10/203,206, filed as application No. PCT/DE01/00470 on Feb. 7, 2001, now abandoned.

(30) Foreign Application Priority Data
Feb. 10, 2000 (DE) ................. 100 06 033

(51) Int. Cl.
*A61K 38/00* (2006.01)
*A61K 35/12* (2006.01)
(52) U.S. Cl. ....................... 514/2; 424/277.1
(58) Field of Classification Search ........ 514/2
See application file for complete search history.

(56) References Cited
U.S. PATENT DOCUMENTS
5,733,920 A 3/1998 Mansuri et al.

FOREIGN PATENT DOCUMENTS

| EP | DE 198 29 473 A | 1/2000 |
|---|---|---|
| WO | WO 98 45444 A | 10/1998 |
| WO | WO 99 02183 A | 1/1999 |
| WO | WO 99/19357 A | 4/1999 |

OTHER PUBLICATIONS

Trisha Gura, "Systems for Identifying New Drugs are Often Faulty", Science, vol. 278, pp. 1041-1042, Nov. 7, 1997.
Matteo Bellone et al., "Cancer Immunotherapy: Synthetic and Natural Peptides in the Balance", Immunology Today, vol. 20, No. 10, pp. 457-461, Oct. 1999.
Alexander Gaiger et al., "Immunity to WT1 in the Animal Model and in Patients With Acute Myeloid Leukemia", Blood, vol. 6, No. 4, pp. 1480-1489, Aug. 15, 2000.
R. Ian Freshney, "Culture of Animal Cells", A Manual of Basic Technique, Alan R. Liss, Inc., New York, p. 4, 1983.
Gerald B. Dermer, "Another Anniversary for the War on Cancer", Bio/Technology, vol. 12, pp. 320, Mar. 1994.
J. H. Carter et al., "Cycling—an Overexpressed Cell Cycle Protein as a Potential Tumour Antigen Target for Immunotherapy", Immunology, vol. 95, No. Suppl. 1, pp. 104, Dec. 1998.

*Primary Examiner*—Christopher H Yaen
(74) *Attorney, Agent, or Firm*—Crowell & Moring LLP

(57) ABSTRACT

The present invention relates to a pharmaceutical composition, comprising a cell cycle regulatory protein and/or an expressible nucleic acid coding for this in an amount suitable for immunization of an individual against carcinomas and the preliminary stages thereof and common auxiliary agents and/or to the use of a cell cycle regulatory protein and/or an expressible nucleic acid coding for this to immunize an individual against carcinomas and the preliminary stages thereof.

2 Claims, No Drawings

SEQUENCE LISTING

```
<160> NUMBER OF SEQ ID NOS: 8

<210> SEQ ID NO 1
<211> LENGTH: 9
<212> TYPE: PRT
<213> ORGANISM: Homo sapiens

<400> SEQUENCE: 1

Val Met Met Met Gly Ser Ala Arg Val
1               5

<210> SEQ ID NO 2
<211> LENGTH: 9
<212> TYPE: PRT
<213> ORGANISM: Homo sapiens

<400> SEQUENCE: 2

Val Leu His Arg Ala Gly Ala Arg Leu
1               5
```

```
<210> SEQ ID NO 3
<211> LENGTH: 9
<212> TYPE: PRT
<213> ORGANISM: Homo sapiens

<400> SEQUENCE: 3

Thr Leu Thr Arg Pro Val His Asp Ala
1               5

<210> SEQ ID NO 4
<211> LENGTH: 9
<212> TYPE: PRT
<213> ORGANISM: Homo sapiens

<400> SEQUENCE: 4

Leu Leu His Gly Ala Glu Pro Asn Cys
1               5

<210> SEQ ID NO 5
<211> LENGTH: 9
<212> TYPE: PRT
<213> ORGANISM: Homo sapiens

<400> SEQUENCE: 5

Ser Met Glu Pro Ser Ala Asp Met Leu
1               5

<210> SEQ ID NO 6
<211> LENGTH: 10
<212> TYPE: PRT
<213> ORGANISM: Homo sapiens

<400> SEQUENCE: 6

Met Met Gly Ser Ala Arg Val Ala Glu Leu
1               5                   10

<210> SEQ ID NO 7
<211> LENGTH: 10
<212> TYPE: PRT
<213> ORGANISM: Homo sapiens

<400> SEQUENCE: 7

Leu Leu Leu His Gly Ala Glu Pro Asn Cys
1               5                   10

<210> SEQ ID NO 8
<211> LENGTH: 10
<212> TYPE: PRT
<213> ORGANISM: Homo sapiens

<400> SEQUENCE: 8

Gly Val Met Met Met Gly Ser Ala Arg Val
1               5                   10
```

IMMUNIZATION OF AN INDIVIDUAL AGAINST CARCINOMAS AND THE PRELIMINARY STAGES THEREOF

This is a continuation of Application Ser. No. 10/203,206, filed Dec. 23, 2002, pending, which is a 371 application of International Application No. PCT/DE01/00470, filed Feb. 7, 2001, which claims priority to DE 100 06 033.1, filed Feb. 10, 2000, all of which are incorporated herein by reference.

The present invention relates to a pharmaceutical composition containing a cell cycle regulatory protein and to the use of the pharmaceutical composition for immunizing an individual against carcinomas and the preliminary stages thereof.

Several million people fall ill with, and die of, carcinomas world-wide every year. These mortality rates have remained unchanged for many years despite intensive therapy research. Until now, patients suffering from carcinomas often have to undergo carcinoma-removing surgery or chemotherapy or radiation therapy. However, this is accompanied by very massive side-effects which then contribute to the mortality rates of patients suffering from carcinomas.

It is thus the object of the present invention to provide a product by means of which therapeutic and prophylactic steps can be taken against carcinomas, the above side-effects being avoided.

According to the invention this is achieved by the subject matters defined in the claims.

The present invention is based on Applicant's findings that in carcinomas or the preliminary stages thereof cell cycle regulatory proteins are available in modified form or amount. For example, overexpression of cyclin-dependent kinase inhibitors is found in carcinomas (cf. Applicant's German patent 198 29 473). Applicant also found out that individuals can be immunized against cell cycle regulatory proteins modified as regards form or amount so as to take therapeutic and prophylactic steps against carcinomas and the preliminary stages thereof. Applicant showed this by way of in vitro and in vivo experiments(cf. below example).

The present invention thus relates to a pharmaceutical composition, comprising a cell cycle regulatory protein and/or an expressible nucleic acid coding for this in an amount suitable for immunization f an individual against carcinomas and the preliminary stages thereof as well as common aixiliary agents.

The employed term "cell cycle regulatory protein" comprises cell cycle regulatory proteins of any kind and origin. For example, these may be cyclins. In particular, these may be cyclin-dependent kinases, such as cdk4 and cdk6, which regulate the cyclins. More particularly, these may be cyclin-dependent kinase inhibitors which, in turn, regulate the cyclin-dependent kinases. Examples of cyclin-dependent kinase inhibitors are the proteins p15, p16, p18, p19, with p16 being preferred. The cell cycle regulatory proteins may be available in wild-type or modified form. The latter form comprises modifications of the amino acid sequence, such as additions, deletions, substitutions and/or inversions of one or more amino acids. Fragments of cell cycle regulatory proteins as such or in combination with carriers may also be present, the fragments being able to have a wild-type or modified amino acid sequence. It is favorable for the carriers in the individual not to be immunogenic. Such carriers may be the individual's own proteins or foreign proteins or fragments thereof. Carriers, such as serum albumin, fibrinogen or transferrin or a fragment thereof are preferred. It is particularly favorable for the fragments of the cell cycle regulatory proteins to contain epitopes which are recognized by cytotoxic T cells, e.g. CD8+ T cells, and may induce a cytotoxic immune response. Such epitopes of cell cycle regulatory proteins can be determined by methods with which a person skilled in the art is familiar, in particular by using an NIH software system (available on the NIH bioinformation service website. It can also be advantageous for different cell cycle regulatory proteins or fragment thereof, to which the above explanations apply correspondingly, to be simultaneously present. For the production of the above cell cycle regulatory proteins, reference is made e.g. to Sambrook et al., Molecular Cloning: A Laboratory Manual, 2nd edition, Cold Spring Harbor Laboratory Press, Cold Spring Harbor N.Y. (1989).

The employed term "expressible nucleic acid coding for a cell cycle regulatory protein" comprises any nucleic acid, e.g. RNA or DNA, expressible in an individual and coding for a cell cycle regulatory protein, to which the above explanations apply correspondingly. The nucleic acid can be present as such, i.e. together with elements suitable for the expression thereof, or in combinaation with a vector. Examples of such elements are promoters and enhancers, such as CMV and SV40, RSV metallothionein I and polyedrin promoter or CMV and SV40 enhancers. Further sequences suitable for expression are disclosed in Goeddel; Gene Expression Technology: Methods in Enzymology 185, Academic Press, San Diego, CA (1990). Moreover, any vectors suitable for expression in mammalian cells can be used as vectors. These are e.g. pcDNA3, pMSX, pKCR, pEFBOS, cDMS and PCEV4 as well as vectors derived from pcDNAI/amp, pcDNAI/neo, pRc/CMV, pSV2gpt, pSV2neo, pSV2-dhfr, pTk2, pRSVneo, pMSG, pSVT7, pSVT7, pko-neo and pHyg. Recombinant viruses, e.g. adenovirus, vaccinia virus or adeno-associated virus, can also be used as vectors. As regards the production of the above nucleic acids, in particular vectors containing such nucleic acids, reference is made to Sambrook, et al., supra, for example.

The employed term "carcinomas and the preliminary stages thereof" comprises carcinomas of any kind and origin and preliminary stages thereof. For example, these may be carcinomas of the upper respiratory tract or anogenital carcinomas, in particular the cervical carcinoma and the preliminary stages thereof, such as cervical intraepithelial neoplasia (CIN I-III), carcinoma in sita (CIS), etc. Likewise benign modifications such as papillomas, adenomas, hyperplasias or similar proliferations of epithelial, mesenchymal or hematopoietic proliferations are also to be counted thereamong.

The employed term "individual" comprises an individual of any kind and origin having cell cycle regulatory proteins and being able to fall ill with carcinomas and/or their preliminary stages. Examples of such individuals are humans and animals as well as cells thereof.

The employed term "amount suitable for immunizaation of an individual" comprises any amount of a cell cycle regulatory protein, to which the above explanations apply correspondingly, or an expressible nucleic acid coding for this, to which the above explanations apply correspondingly, and with which an individual can be immunized. The amount depends on whether a cell cycle regulatorky protein or an expressible nucleic acid coding for this is used. The amount also depends on whether immunization of the individual rather aims at an induction of antibodies directed against modified cell cycle regulatory proteins or a stimulation of cytotoxic T cells, e.g. CD8+ T cells, directed against modified cell cycle regulatory proteins. Both possibilities of immunization can be achieved by the present invention. Furthermore, the amount depends on whether immunization is intended as a prophylacaric or therapeutic treatment. In addition, the individual's age, sex and weight play a role for determining the amount. It is favorable to give the indivdual 100 μg–1 g of a cell cycle regulatory protein or $10^6$–$10^{12}$ MOI of a recombinant virus containing an expressible nucleic acid coding for a cell cycle regulatory protein by means of injection. The injection may be made at various sites of the individual intramuscularly, subcutaneously, intradermally or in any other form of application. It may also be favorable to carry out one or more "booster injections" having about equal amount. In this case, it may be particularly favorable to use different fragments of the respective cell cycle regulatory proteins for the individual injections.

The employed term "common auxiliary agents" comprises any auxiliary agents suitable for a pharmaceutical composition to immunize an individual. Such auxiliary agents are e.g. immunization adjuvants, such as GM-CSF or Freund's adjuvant, buffered common salt solutions, water, emulsions, such as oil/water emulsions, wetting agents, sterile solutions, etc.

By means of the present invention it is possible to immunize individuals, in particular humans and animals, against midified cell cycle regulatory proteins. Immunization takes place by both induction of antibodies and stimulation of $CD8^+$ T cells, directed against modified cell cycle regulatory proteins. Thus, it is possible to tske prophylactic and therapeutic steps against carcinomas and the preliminary stages thereof.

The invention is explained by the below example.

Example

Stimulation of $CD8^+$ T cells against the cyclin-dependent kinase inhibitaor p16 and lysis of p16-overexpressing carcinoma cells.

(A) Stimulation of $CD8^+$ T cells against p16.

Peripheral mononuclear cells are obtained from a healthy donor and subjected to what is called ELISPOT analysis. It is the principle of this experiment to stimulate lymphocytes in culture vessels with specific antigen, Whenever the lymphocytes are activated as they recognize the antigen,the activated lymphocytes release cytokines which, in turn, bind to specific antibodies immobilized on the bottom surface of the culture vessels. Having washed out the lymphocytes, the bound cytokines can be detected in the culture vessels by means of a second antibody made visible in a subsequent color reaction.

Peripheral blood lymphocytes (PBL) from an HLA-A0201-positive healthy proband are purified by density centrifugation via a Ficoll Paque®gradient. T-lymphocytes are obtained by separating the B-lymphocytes or the monocytes using antibody-coupled magnetobeads (CD11, CD16, CD19, CD36 and CD56) (Pant T cell isolation Kit®, Milteny, Bergisch Gladbach, Germany). About $2\times10^7$ T cells are obtained from 30 ml blood.

HLA-A0201-restricted peptides of p16 are identified by means of an NIH software system (available on the_NIH bioinformation service). These are the below peptides: TABLE-US-00001 9 mer peptides: 10 mer peptides: score 1: VMMMGSARV (SEQ ID NO:1) score 1: MMGSARVAEL (SEQ ID NO:6) score 2: VLHRAGARL (SEQ ID NO:2) score 2: LLLHGAEPNC (SEQ ID NO:7) score 3: TLTR-PVHDA (SEQ ID NO:3) score 3: GVMMMGSARV (SEQ ID NO:8) score 4: LLHGAEPNC (SEQ ID NO:4) score 5: SMEPSADML (SEQ ID:5)

The isolated T cells are incubates withn T2 cells, which (a) have been loaded with a mixture of the above 9 mer peptides (10 µg/peptide) and (b) with a mixture of the above 10 mer peptides (10 µg/peptide). The T cells are restimulated once a week for a period of 6 weeks. $10^7$ T cells each are cocultured with $2\times10^6$ peptide-loaded T2 cells in 24-well plates.

The reactivity over the peptide-loaded T2 cells is determined once a week, starting on day 0 of the experiment, by carrying out IFN-.gamma. elispot analysis. On day 28, a reactivity is observed by the mixture of (a) (400 specific cells per million cells). The main reactivity is in this case directed against the peptide VMMMGSARV (SEQ ID NO:1) (1,000 specific cells/1,000,000 cells) (FIG. 1). A less intensive activity is observed against the mixture of (b) (150 specific cells/1,000,000 ). Here, the peptide MMGSARVAEL (SEQ ID NO:6) shows maximum reactivity (600 specific cells/1,000, 000 cells).

Hence it is evident that it is possible to stimulate $CD8^+$ T cells activated against p16.

(B) Lysis of p16-overexpressing carcinoma cells

Following another restimulation, the activated $CD8^+$ T cells are incubated with the HLA A0201+ cervical carcinoma cells Caski, which overexpress p16. The colon carcinoma cells SW480 which do not overexpress p16 are used as controls. $10^6$ Caski cells are labeled with $^{52}Cr$ (100 µCi) at 37° C. for 1 h and cocultured with increasing numbers of activated $CD8^+$ T cells for 3 hours. Specific lysis of the Caski cells is determined by the amount of released radioactivity in supernatant.

It turns out that Caski cells are lyzed by the activating $CD8^+$ T cells but Not by the controll cells SW480 (figure 2).

The invention claimed is:

1. A method for immunizing against carcinomas and the preliminary stages thereof, comprising use of fragments of a cyclin-dependent kinase inhibitor, wherein the carcinomas are those of the upper respiratory tract and/or anogenital carcinomas, wherein the cyclin-dependent kinase inhibitor is a protein p16; and wherein the fragment or fragments contain epitopes which can be detected by cytotoxic T cells and elicit a cytotoxic immune response.

2. The method of claim 1, wherein the anogenital carcinoma is a cervical carcinoma.

* * * * *